United States Patent
Wang

(10) Patent No.: US 6,928,319 B2
(45) Date of Patent: Aug. 9, 2005

(54) ACUPUNCTURE DEVICE

(76) Inventor: Shao-Hua Wang, 5F-1, No. 8, Section 3, Shuang-shr Road, Banchiau (TW)

( * ) Notice: Subject to any disclaimer, the term of this patent is extended or adjusted under 35 U.S.C. 154(b) by 141 days.

(21) Appl. No.: 10/159,018

(22) Filed: Jun. 3, 2002

(65) Prior Publication Data

US 2004/0015213 A1 Jan. 22, 2004

(51) Int. Cl.$^7$ ................................................ A61N 1/18
(52) U.S. Cl. .............................. 607/2; 607/46; 607/148; 128/907
(58) Field of Search ............................... 607/2, 46, 48, 607/50, 68–72, 74, 142, 148; 128/907

(56) References Cited

U.S. PATENT DOCUMENTS 4,895,153 A * 1/1990 Takeuchi et al. .............. 607/50
5,269,304 A * 12/1993 Matthews .................... 607/46

* cited by examiner

Primary Examiner—Jeffrey R. Jastrzab

(57) ABSTRACT

This invention is an improved acupuncture device comprising of several cartridges (including a control circuit, a power supply unit, and a power switch in each cartridge) and leads among cartridges. Each cartridge has a conductive clip, which can lock a picking onto the cartridge. Open the power switch to power on the control circuit, and the current will flow to the picking through the clip. Stamp the picking onto an acupoint to excite it with the low frequency current generated by the control circuit. In this way, the device can result in the same effect as needle therapy. Furthermore, due to the flexibility of the leads, the device can be applied on multi acupoints.

2 Claims, 5 Drawing Sheets

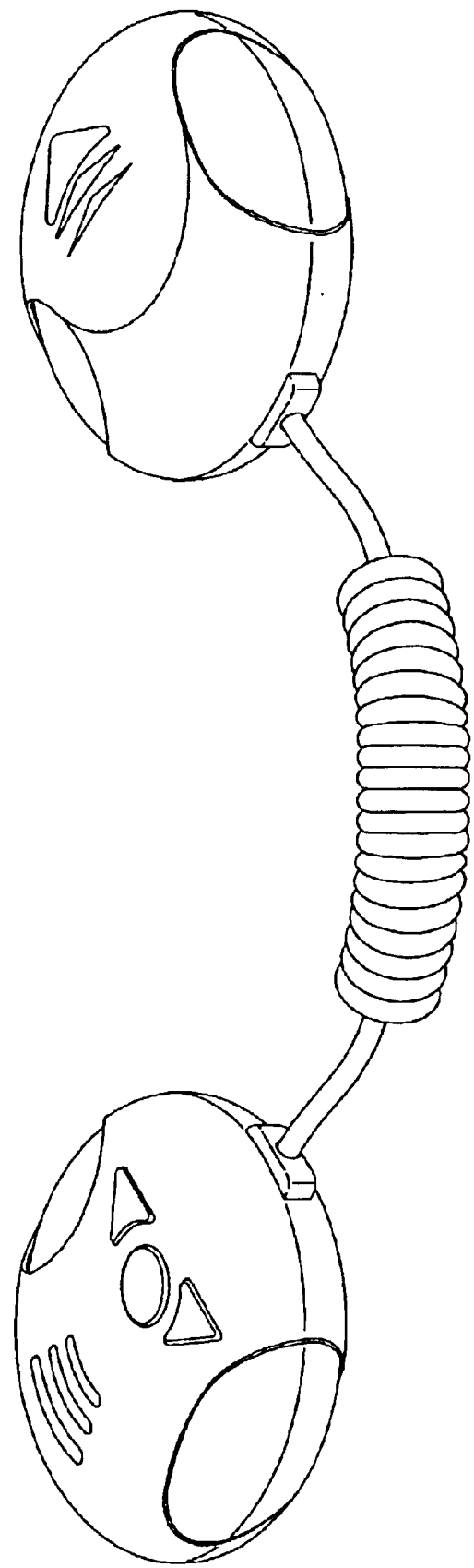

ACUPUNCTURE DEVICE

FIELD OF THE INVENTION

This invention provides an improved acupuncture device, in particular refers to an acupuncture device simple in structure, portable, and easy to use.

BACKGROUND OF THE INVENTION

Legacy acupuncture devices generate treatment and health care effect through puncture acupoints with needles. However, they have the following shortcomings or disadvantages:
1. hard to apply due to the profound expertise;
2. limited to specific environments due to the sanitization process of acupuncture devices;
3. not suitable for timid persons or children due to the potential fear felling resulted from needles.

Consequently, some electronic acupuncture devices fulfilling the treatment or health care through exciting acupoints with low frequency current. The principle of this therapy is to excite the nerve fibers in man body with the low frequency electric current to agitate the "nerve induced current", which has the same waveform as that of the electric current. The structure of a typical acupuncture device mentioned above comprises of a power supply unit and one or more lead extending from the power supply unit to connect to a needle or picking at the other end of each lead. Place the needle or picking on an acupoint, and the device can generate the same therapeutic effect as needle therapy. Though such an acupuncture device is simple in operation, it still has the following shortcomings:
1. The lead extending from the device may entangle with each other, which may not only result in inconvenience in operation but also failure;
2. Not portable due to its large size;
3. Expensive due to its complicity in structure;
4. May result in failure and hard maintenance work due to the complicity of its circuit.

SUMMARY OF THE INVENTION

In consideration of the disadvantages and shortcomings of traditional acupuncture devices (including needle therapy and above electric acupuncture devices), the inventor develops an improved acupuncture device, in particular refers to an acupuncture device simple in structure, portable, easy to use, and the most important, with flexible leads to extend the applying area of this device.

The main purpose of this invention is to provide an improved acupuncture device, which is simple in structure and easy to use.

Another purpose of this invention is to provide an improved acupuncture device, which is lightweight and portable.

Another purpose of this invention is to provide an improved acupuncture device, which is simple in structure and easy to maintain.

Another purpose of this invention is to provide an improved acupuncture device, which is powered with DC batteries, thus economical.

BRIEF DESCRIPTION OF THE DRAWINGS

FIG. 6 is a further embodiment of the present invention.

INSTRUCTION OF THE REFERENCE NUMBERS

10 Cartridge

| | |
|---|---|
| 11 | Top Cover |
| 111, 112 | Button |
| 1111, 1121 | Hole |
| 1112, 1122 | Bulgy Pole |
| 113, 114 | Bulgy Pole |
| 115, 116 | Hole |
| 12 | Bottom Cover |
| 121 | Bulgy Structure |
| 122, 123 | Pole |
| 124 | Bulgy Pole |
| 13 | Screw |
| 14 | Control Circuit |
| 141, 142 | Switch |
| 15 | Sleeve Unit |
| 16 | Bulgy Button |
| 161 | Sleeve Ear |

20 Cartridge

| | |
|---|---|
| 21 | Top Cover |
| 211 | Battery Cell |
| 2111 | Hole |
| 2112 | Narrower Hole |
| 212 | Outer Cover |
| 2121 | Pin |
| 213, 214 | Conductive Plate |
| 22 | Bottom Cover |
| 221 | Bulgy Structure |
| 222, 223 | Pole |
| 224 | Bulgy Pole |
| 23 | Screw |
| 25 | Sleeve Unit |
| 251, 252 | Sleeve |
| 26 | Concave Button |
| 261 | Sleeve Ear |
| 30 | Electric lead |
| 40, 50 | Picking |
| 41, 51 | Bulgy Button |
| 60 | Battery |

DETAILED DESCRIPTION OF THE PREFERRED EMBODIMENTS

The additional purposes and structure of this invention will be further elucidated as follows. Some parts or the arrangement of parts of this invention in different embodiments may be slightly different. However, the embodiments selected in this document will be detailed and illustrated to make the technologies used in this invention more clear.

Figure 1:
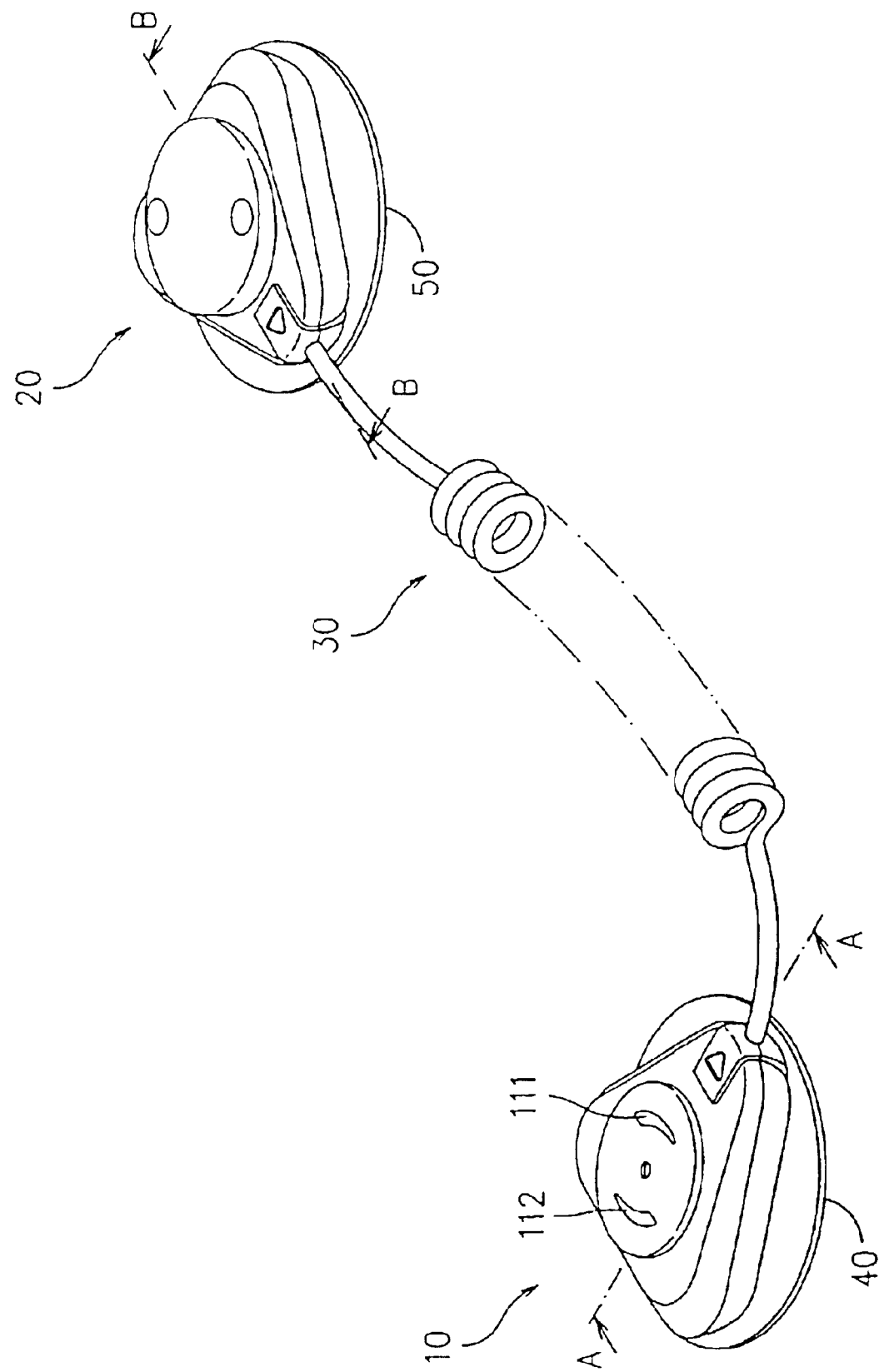
FIG. 1 is the 3D view of this invention.

Please see the improved acupuncture device in FIG. 1, wherein the device mainly comprises of two cartridges (10 and 20), electric leads (30) between cartridge 10 and 20, and adhesive picking 40 and 50 at the bottom of cartridge 10 and 20.

Figure 2:
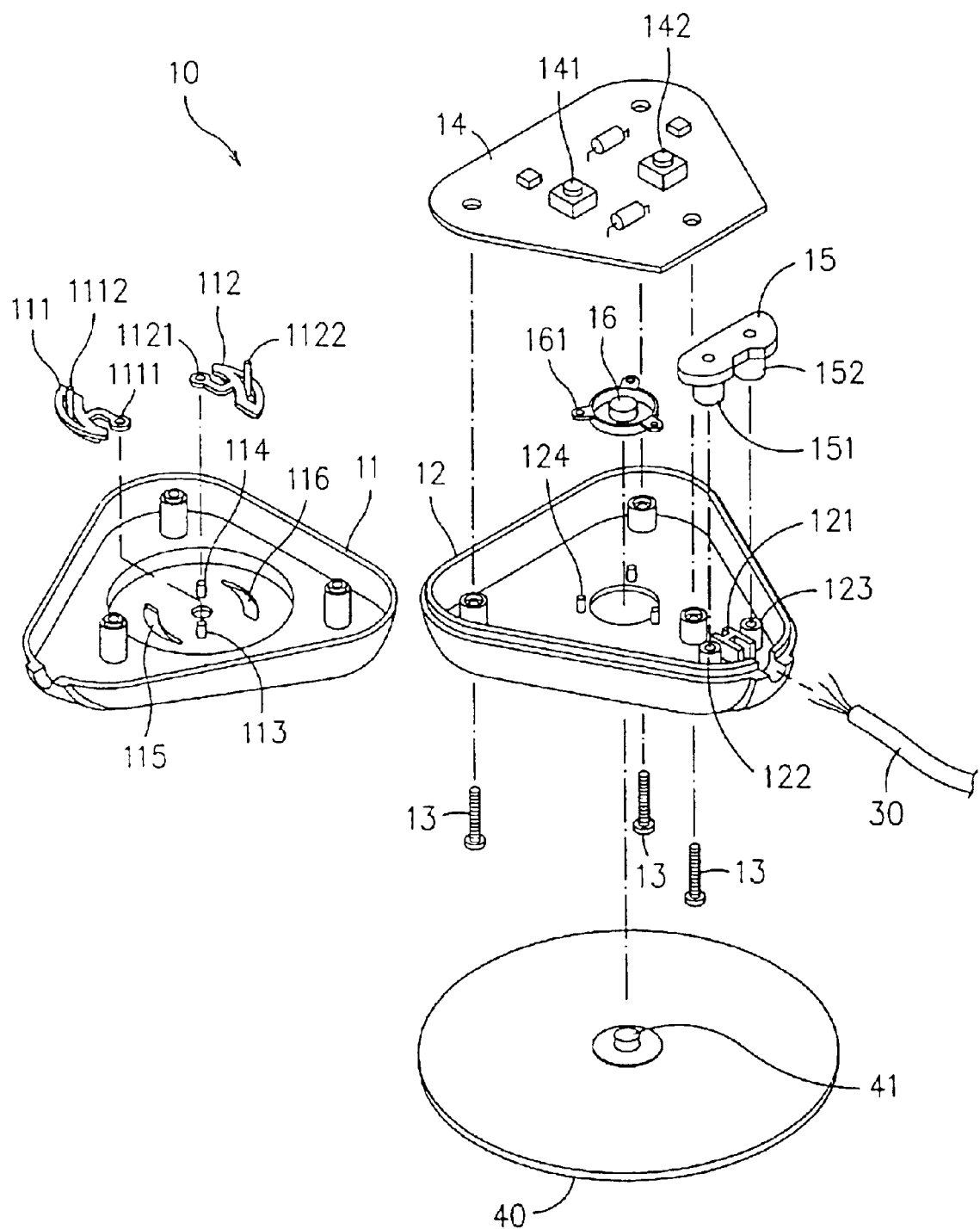
FIG. 2 is an exploded 3D view of this invention (with the control circuit and cartridges).
Figure 4:
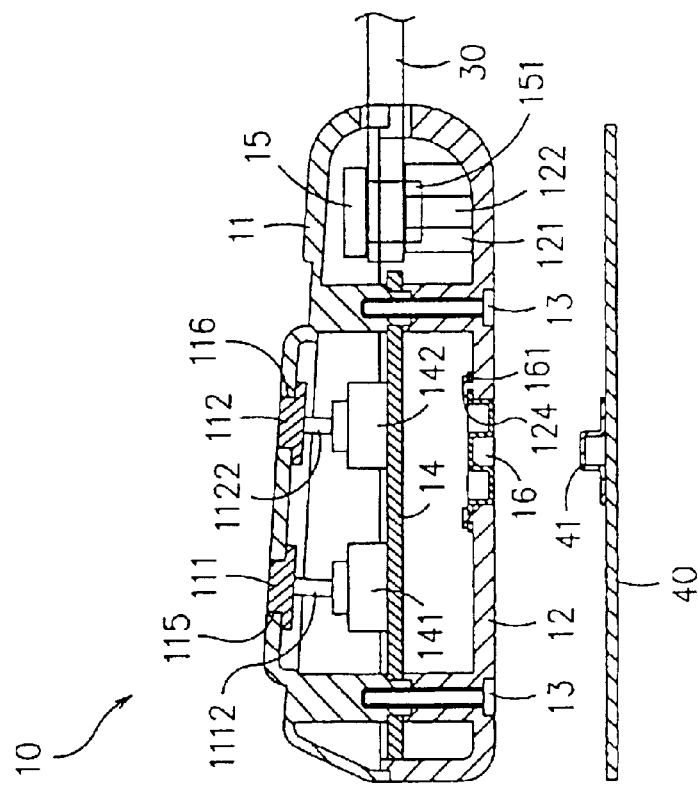
FIG. 4 is a sectional view of FIG. 1 along A—A line.

Please see FIG. 2 and FIG. 4, wherein the cartridge 10 is composed of a top cover (11) and a bottom cover (12), and the two covers can be locked together with a screw (13).

There is a bulgy structure (121) at the position of the electric lead (30) on bottom cover 12. At each side of the bulgy structure 121 there is a pole (122 and 123), respectively, which is slightly higher than bulgy structure 121 there is a "∩" shape unit (15) on pole 122 and 123, respectively, and each "∩" shape unit (15) has a sleeve (151 and 152), which can be fit over pole 122 and 123. There is a free space between "∩" shape unit (15) and bulgy structure 221 for the lead 30 to pass through and be clamped there.

There is a control circuit (14) in cartridge 10, connecting electric lead 30. On top cover 11, there are two buttons (111 and 112) passing through hole 1111 and 1121 and fixed on bulgy pole 113 and 114, which are fused and compressed together to fix pole 1111 and 1121 and form a free space in hole 115 and 116. Button 111 and button 112 face against switch 141 and 142 on the control circuit 14. Press button 111 and 112 to make bulgy pole 1112 and 1122 at the bottom contact with switch 141 and 142 to control these switches.

There is a conductive clip between top cover 12 and picking 40. The conductive clip can be any form, but the buckle structure (bulgy button 41 and concave button 16) in the figure is the simplest and easy to implement. In this case, the bulgy button 41 is pressed on picking 40, and the concave button 16 is fit over the bulgy pole 124 on bottom cover 12 with sleeve ear 161, The bulgy pole is fused and compressed to fix sleeve ear 161, which in turn fix concave button 16 on the bottom of bottom cover. The clip unit composed of bulgy button 41 and concave button 16 can press picking 40 with cartridge 10 together.

Figure 3:
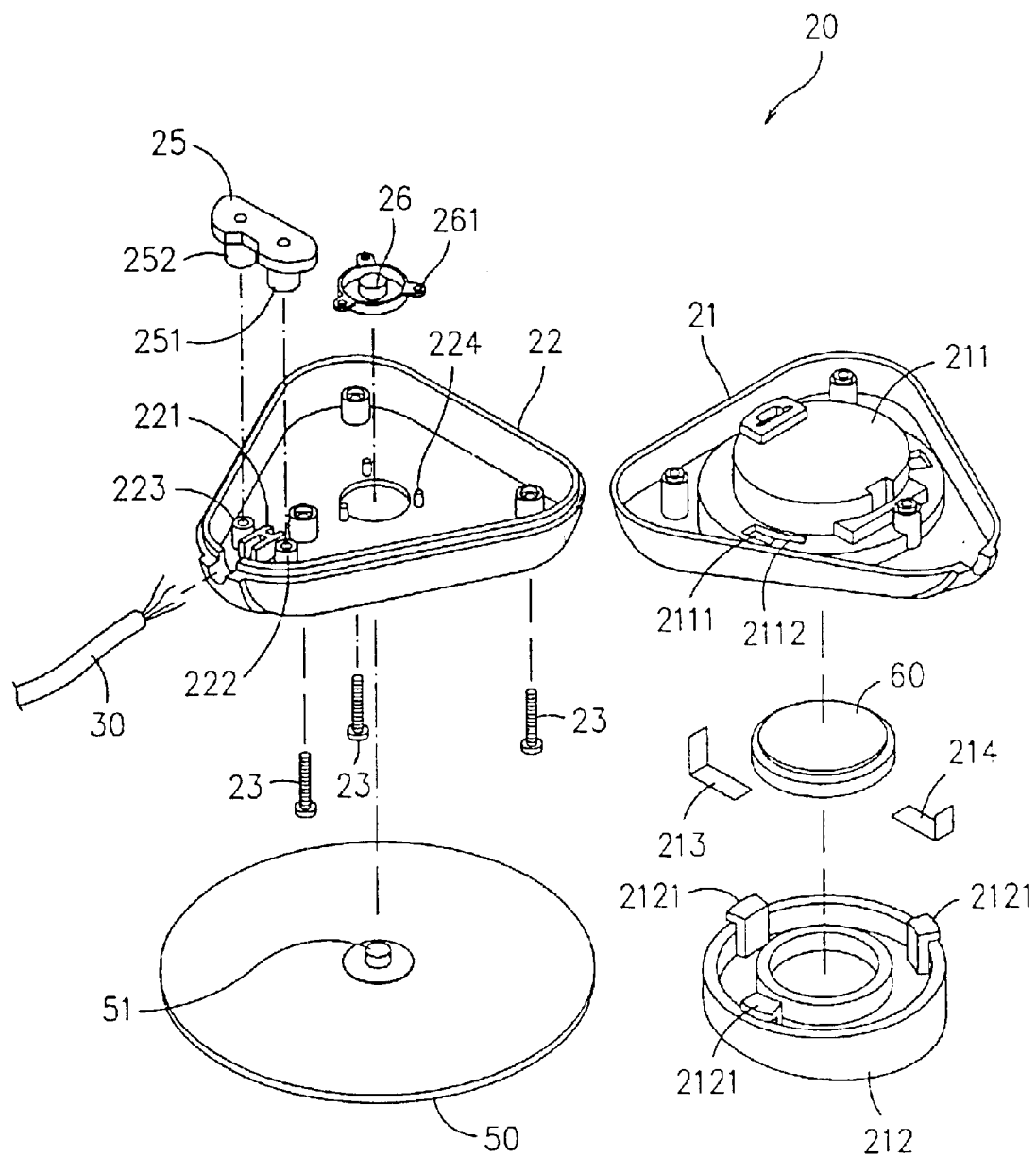
FIG. 3 is an exploded 3D view of the invention (with the power supply unit and cartridges).
Figure 5:
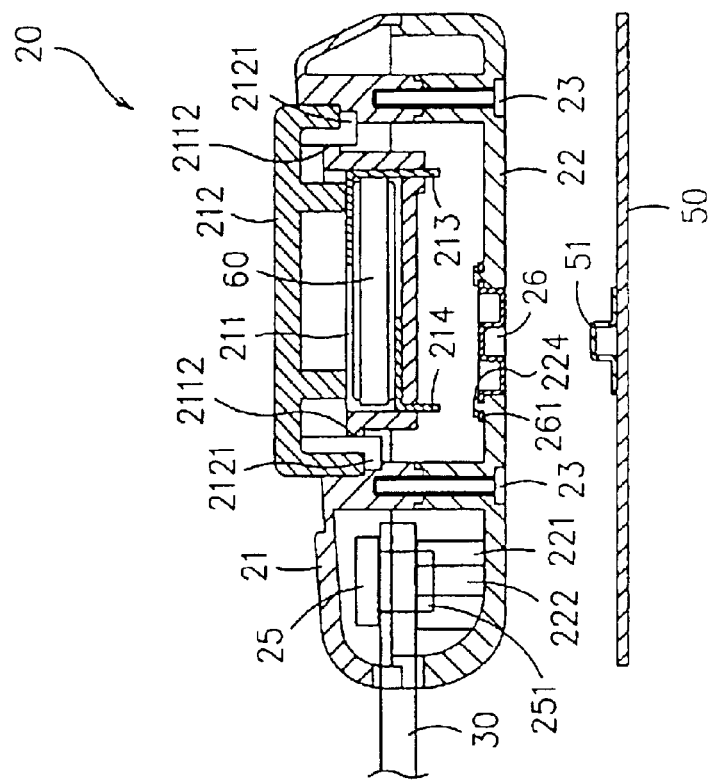
FIG. 5 is a sectional view of FIG. 1 along B—B line.

Please see FIG. 3 and FIG. 5, wherein the cartridge 20 is composed of a top cover (21) and a bottom cover (22), and the two covers can be locked together with a screw (23).

Similar to the bottom cover 12 of cartridge 10, there is a bulgy structure (221) at the position of the electric lead (30) on bottom cover 22. At each side of the bulgy structure 221 there is a pole (222 and 223), respectively, which is slightly higher than bulgy structure 221, there is a "∩" shape unit (25) on pole 222 and 223, respectively, and each "∩" shape unit (25) has a sleeve (251 and 252), which can be fit over pole 222 and 223. There is a free space between "∩" shape unit (25) and bulgy structure 221 for the lead 30 to pass through and be clamped there.

There is a battery cell (211) and an outer cover (212) on top cover 21. The outer cover 212 has an "L" shape pin 2121. Push pin 2121 into the hole (211) against battery cell 211) clamp it into the narrower hole 2112, and then the outer cover can be fixed, the battery (60) can be locked in battery cell 21 as well. There are two conductive plates (213 and 214) in battery cell 211, contacting with the positive and negative pole of the battery, respectively. Conductive plate 213 and 214 extend into the bottom cover 22 and connect with electric lead 30.

Similar to the bottom cover 12 of cartridge 10, there is a conductive clip between top cover 22 and picking 50. The conductive clip can be any form, but the buckle structure (bulgy button 51 and concave button 26) in the figure is the simplest and easy to implement. In this case, the bulgy button 51 is pressed on picking 50, and the concave button 26 is fit over the bulgy pole 224 on bottom cover 22 with sleeve ear 261. The bulgy pole is fused and compressed to fix sleeve ear 261, which in turn fix concave button 26 on the bottom of bottom cover 22. The clip unit composed of bulgy button 11 and concave button 26 can press picking 50 with cartridge 20 together.

Please see FIG. 1 again. When picking 40 and 50 are clamped together with 10 and 20, respectively, they can be place at two acupoints on man body. The distance between cartridge 10 and 20 depends on the length of the lead 30 (as shown in the figure). Stamp picking 40 and 50 at two acupoints on man body and add power to them by switching on button 111 and 112, the device can generate the same therapeutic effect as needle therapy with low frequency current controlled by the control circuit.

From above description we can see this invention can attain above purposes and meets all requirements for applying for a patent. According to the regulation ("Solving new problems with a existing method, or solving existing problems with a new method can be regarded as an innovation; an innovation with a new structure can be qualified for applying for a new patent, even through it is not new in principle") of the Patent Office, I apply for a new patent with it.

Above description and illustration are only for the said embodiments and should not constitute a limitation in applying for a new patent. In cases they are not suitable for confine the actual applying range of this invention, any implementation with the structure and functionality described above but some alternation in figure or equivalent components should fall in the concept of this invention.

What is claimed is:

1. An improved acupuncture device, comprising:

a first cartridge, being formed with a first top cover and a first bottom cover, the first top cover fixedly attached to the first bottom cover and having two holes fitting with a button respectively and the first bottom cover providing a central hole being fixedly attached with a first conductive clip member;

a control circuit, being fixedly attached in the first cartridge and providing two switches corresponding the respective button so as to be contacted with the buttons;

a second cartridge, being formed with a second top cover and a second bottom cover, the second top cover fixedly attached to the second bottom cover and providing a battery cell, an outer cover being attached to the battery cell and the second bottom cover providing a central hole being fixedly attached with a second conductive clip member;

a battery, being received in the battery cell of the second cartridge and attached to a positive pin and a negative pin;

two pickings, each of the pickings having a conductive part and being attached to the first clip member and second clip member respectively; and an extendable electric lead with two ends, one of the two ends being electrically connected to the control circuit via the first bottom cover and the other one of the two ends being electrically connected to the battery via the second bottom cover.

2. The improved acupuncture device as defined in claim 1, wherein the first bottom cover and the second bottom cover respectively provide a bulgy part with two lateral sides thereof next to a pole respectively and an inversed U shaped sleeve unit provides two sleeves fitting, with the poles such that a space between the bulgy part and the sleeve unit for the two ends of the lead passing through and being clamped.

* * * * *